(12) United States Patent
Hung et al.

(10) Patent No.: US 6,282,940 B1
(45) Date of Patent: Sep. 4, 2001

(54) APPARATUS FOR TESTING CARBON MONOXIDE ALARMS

(75) Inventors: Patrick F. C. Hung, Tsuen Wan N.T. (HK); James C. K. Chan, Unionville (CA)

(73) Assignee: Patrick Plastics Inc., Vaughan (CA)

( * ) Notice: Subject to any disclaimer, the term of this patent is extended or adjusted under 35 U.S.C. 154(b) by 0 days.

(21) Appl. No.: 09/326,569

(22) Filed: Jun. 7, 1999

(51) Int. Cl.$^7$ .................................................. G01N 27/407
(52) U.S. Cl. ............................................. 73/1.06; 340/515
(58) Field of Search ..................... 73/1.06, 1.02; 340/515

(56) References Cited

U.S. PATENT DOCUMENTS

| | | |
|---|---|---|
| 3,242,715 * | 3/1966 | Hubner .................................. 73/1.03 |
| 4,271,693 | 6/1981 | Bute . |
| 4,306,575 | 12/1981 | Minozzi, Jr. . |
| 4,384,925 * | 5/1983 | Stetter et al. ........................ 73/1.07 |
| 4,462,244 | 7/1984 | Lee . |
| 5,523,744 | 6/1996 | Wieser . |
| 5,659,125 * | 8/1997 | Ernst ..................................... 73/1.03 |
| 5,959,188 * | 9/1999 | Deutsch et al. ....................... 73/1.06 |
| 6,098,523 * | 8/2000 | Warburton ............................ 73/1.06 |

FOREIGN PATENT DOCUMENTS

| | | |
|---|---|---|
| 3721671 * | 7/1988 | (DE) . |
| 127149 * | 10/1980 | (JP) . |

* cited by examiner

*Primary Examiner*—Hezron Williams
*Assistant Examiner*—Nashmiya Fayyaz
(74) *Attorney, Agent, or Firm*—Bereskin & Parr

(57) ABSTRACT

Apparatus for testing the operation of a carbon monoxide alarm of the type having a casing and a CO sensor extending therefrom, includes a housing sized and configured to receive the casing and to form a gas chamber in communication with the sensor, a source of CO gas, comprising a flammable substance which generates CO gas when burned, and a holder located within the housing for holding the source while the source is being burned. The CO source generates a concentration of carbon monoxide gas within the chamber which is above a pre-selected threshold for a sufficient period of time to trigger an alarm condition.

7 Claims, 8 Drawing Sheets

APPARATUS FOR TESTING CARBON MONOXIDE ALARMS

FIELD OF THE INVENTION

This invention relates to apparatus for testing the operation of carbon monoxide alarms.

BACKGROUND OF THE INVENTION

Carbon monoxide alarms are now recommended or required for use in residential houses in many jurisdictions in North America, particularly for houses which are heated by natural gas or oil furnaces. Carbon monoxide alarms typically comprise a CO (carbon monoxide) sensor and associated electronics housed in a compact casing, which may be ac or battery operated. CO alarms are designed to respond when the concentration of carbon monoxide exceeds certain preset values over preselected periods of time. For example, the Underwriters Laboratories Standard UL 2034, based upon 10 percent carboxyhemoglobin, requires a CO alarm to sound when the CO concentration exceeds 70 ppm (parts per million) for 240 minutes, or 150 ppm for 50 minutes, or 400 ppm for 15 minutes.

Carbon monoxide alarms are reliable, and they typically include test circuits which allow the consumer to test the electronics. Nevertheless, many consumers have expressed a desire to satisfy themselves that the CO alarm will generate an alarm signal, in the presence of a harmful concentration of carbon monoxide gas.

Consumers have been known to "test" CO alarms by placing them adjacent the exhaust pipe of an automobile, for a period of time. However, this form of testing is generally not effective, since automobile exhaust gas is dirty, and tends to contaminate the CO sensor.

There is a CO alarm testing kit currently available in the marketplace, comprising a glass vial of CO gas and a plastic bag. To test an ac operated CO alarm using this testing kit, the user must plug the alarm into an extension cord, place the alarm and the vial into the bag, close the bag around the extension cord, and break the vial. This testing kit is not always effective, because sometimes the vial leaks, and it is difficult to determine if the vial is full or empty, because CO gas is colourless. This kit is somewhat awkward for use with ac operated alarms, since it requires the user to hold the bag tightly around the extension cord for a period of time. This kit is also relatively expensive, and can be used only once.

There is accordingly a need for an improved CO alarm testing device, which overcomes the disadvantages of the prior art.

SUMMARY OF THE INVENTION

The present invention is directed towards test apparatus for testing the operation of a carbon monoxide alarm of the type having a casing and a CO sensor extending therefrom. The test apparatus comprises a housing sized and configured to receive the casing and to form a gas chamber in communication with the sensor, a CO source for generating a concentration of carbon monoxide within the chamber above a pre-set threshold level for a sufficient period of time to trigger an alarm condition, comprising a flammable material which generates carbon monoxide gas when burned, and a holder located within the housing for holding the source while the source is burned.

The housing preferably comprises walls sized and configured to provide a friction fit around the casing of the alarm. The source of CO gas is preferably a charcoal pellet or small stick of incense. The holder preferably comprises a metal fire box sized to receive the CO source, and support means extending into the gas chamber from a wall of the housing having a slot shaped for receiving the fire box. In one embodiment, the housing comprises a portion of the packaging for the CO alarm.

BRIEF DESCRIPTION OF THE DRAWINGS

The invention will now be described, by way of example only, by reference to the following drawings, in which.

DETAILED DESCRIPTION OF THE PREFERRED EMBODIMENTS

Figure 1:
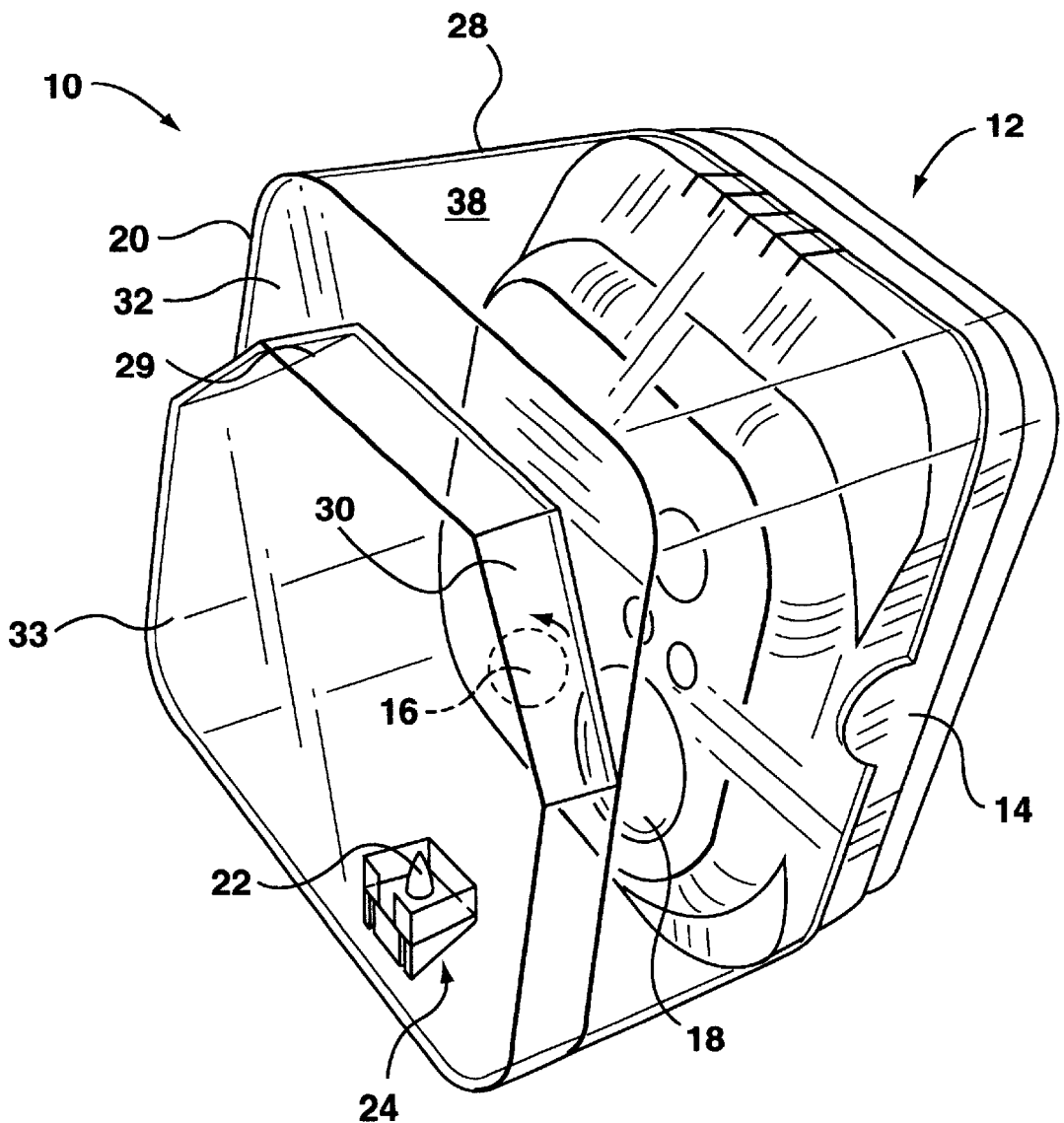
FIG. 1 is a perspective view of a testing apparatus made in accordance with a preferred embodiment of the invention, shown fitted onto a CO alarm.
Figure 2:
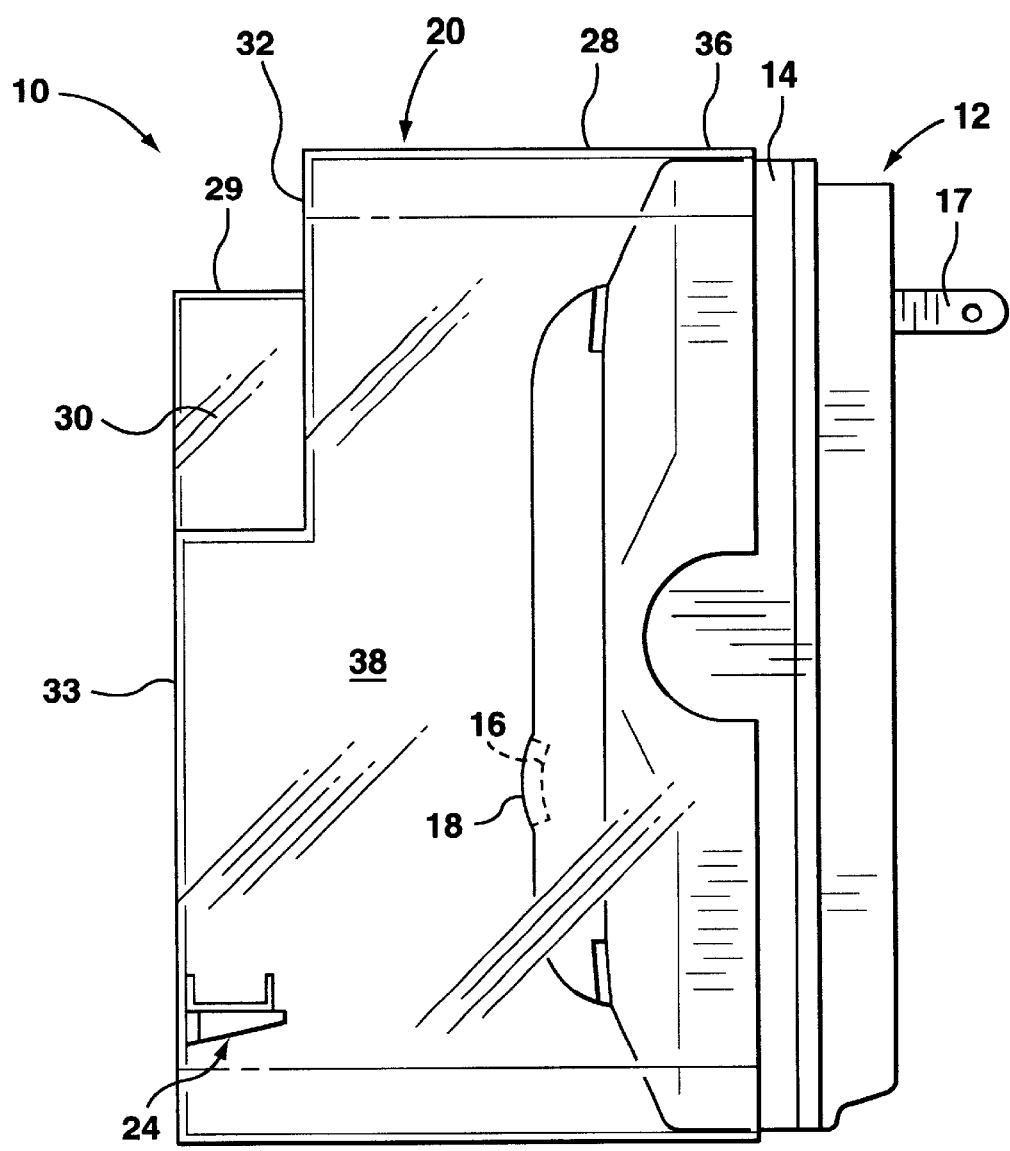
FIG. 2 is a side elevational view of the preferred embodiment.

Referring to FIGS. 1 and 2, illustrated therein is a CO alarm testing apparatus 10 made in accordance with a preferred embodiment of the subject invention. Testing apparatus 10 is shown fitted onto a conventional 120 volt ac operated CO alarm 12 comprising a generally square casing 14 having CO sensor 16 mounted in the front wall thereof, plug 17 extending from the back wall and piezoelectric buzzer 18 which emits audible alarm signals when the CO concentration exceeds certain specified limits for certain specified time durations.

Test apparatus 10 comprises housing 20, CO gas source 22, and source holder 24.

Housing 20 comprises sidewalls 28, 29 and 30, and integral front walls 32, 33 which together form an enclosure having an open back. Back ends 36 of sidewalls 28 are sized and shaped to form a friction fit around the periphery of alarm casing 14. When housing 20 is fitted onto casing 14, housing 20 forms a gas chamber 38 surrounding alarm sensor 16. The fit between housing 20 and casing 14 need not be air tight. Housing 20 is preferably made of a clear plastic such as polystyrene or polyproplyene. Housing 20 may be vacuum formed or injection moulded.

CO gas source 22 comprises an inflammable substance which, when ignited, smolders and generates CO gas over a period of time. CO source 22 is preferably a pellet of charcoal or small stick of incense, and may comprise other burnable substances such as a piece of wood or cigarette. These substances are abundant, easily obtainable, and inexpensive.

Figure 3:
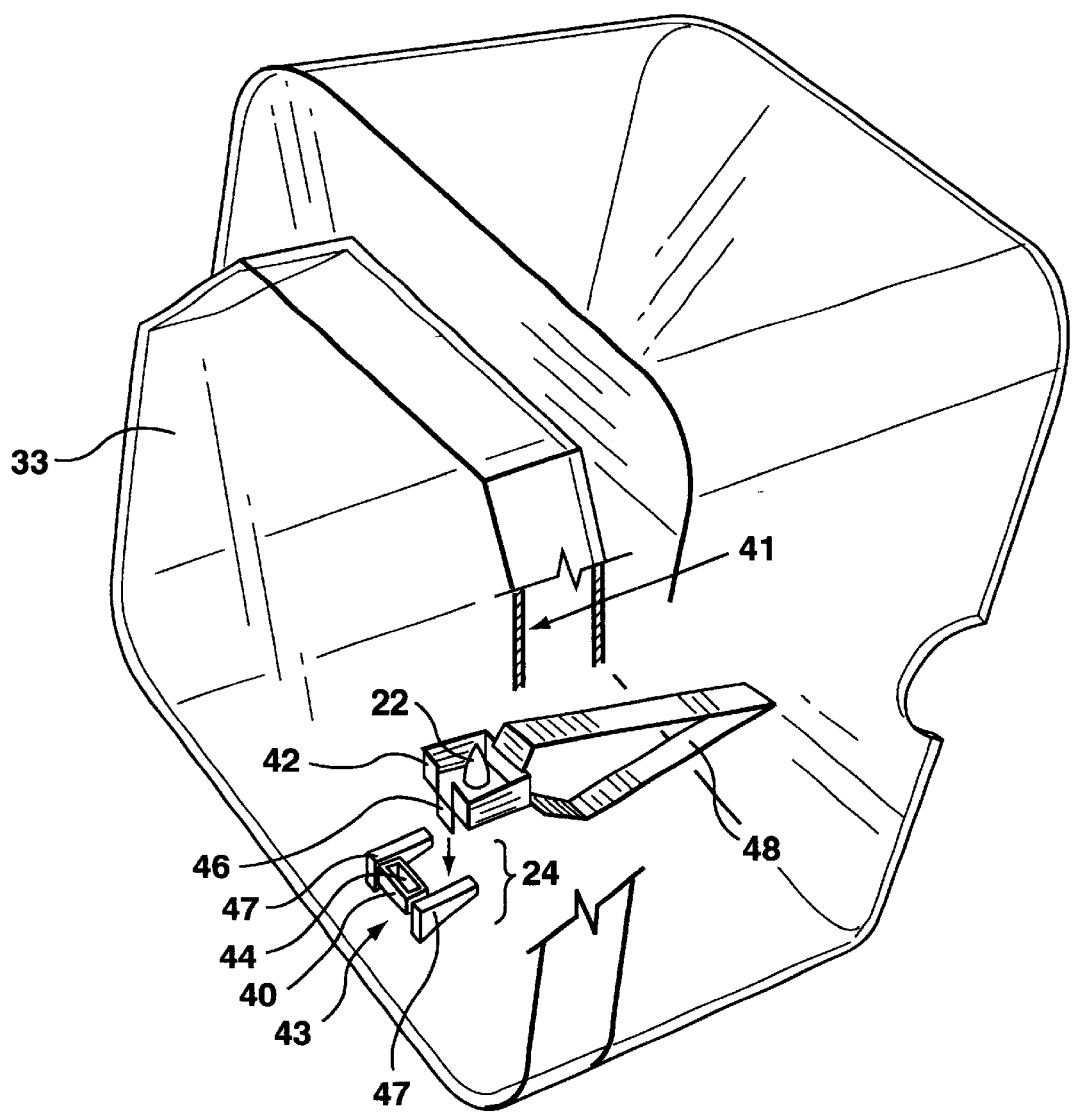
FIG. 3 is a partially cut-away perspective view of the preferred embodiment, showing the CO source holder being put into place by tongs.

As best shown in FIG. 3, source holder 24 comprises a metal fire box 42 sized to hold CO source 22, and support means 43 for supporting fire box 42, extending into gas chamber 38 from the inside surface 41 of front wall 33. Support means 43 comprises protrusion 40 extending horizontally along inside surface 41, having slot 44, and support brackets 47 located on either side of slot 44. Fire box 42 has a front tab 46 sized to be inserted into slot 44. Front wall 33 must be rigid enough to support the weight of fire box 42 and CO source 22. Fire box 42 may be pre-installed in slot 44 by the factory, or inserted into slot 44 by the user. Apparatus 10 preferably include tongs 48 which can be used to hold CO source 22 while it is being ignited, and to insert burning CO source 22 into fire box 42.

As CO source 22 is burned, oxygen in the air within chamber 38 is converted into CO. Housing 20 must accordingly be sized relative to CO source 22 to ensure that gas chamber 38 contains enough oxygen for CO source 22 to generate a concentration of carbon monoxide gas above a pre-specified threshold volume for a long enough period of time to trigger an alarm condition.

Figure 4:
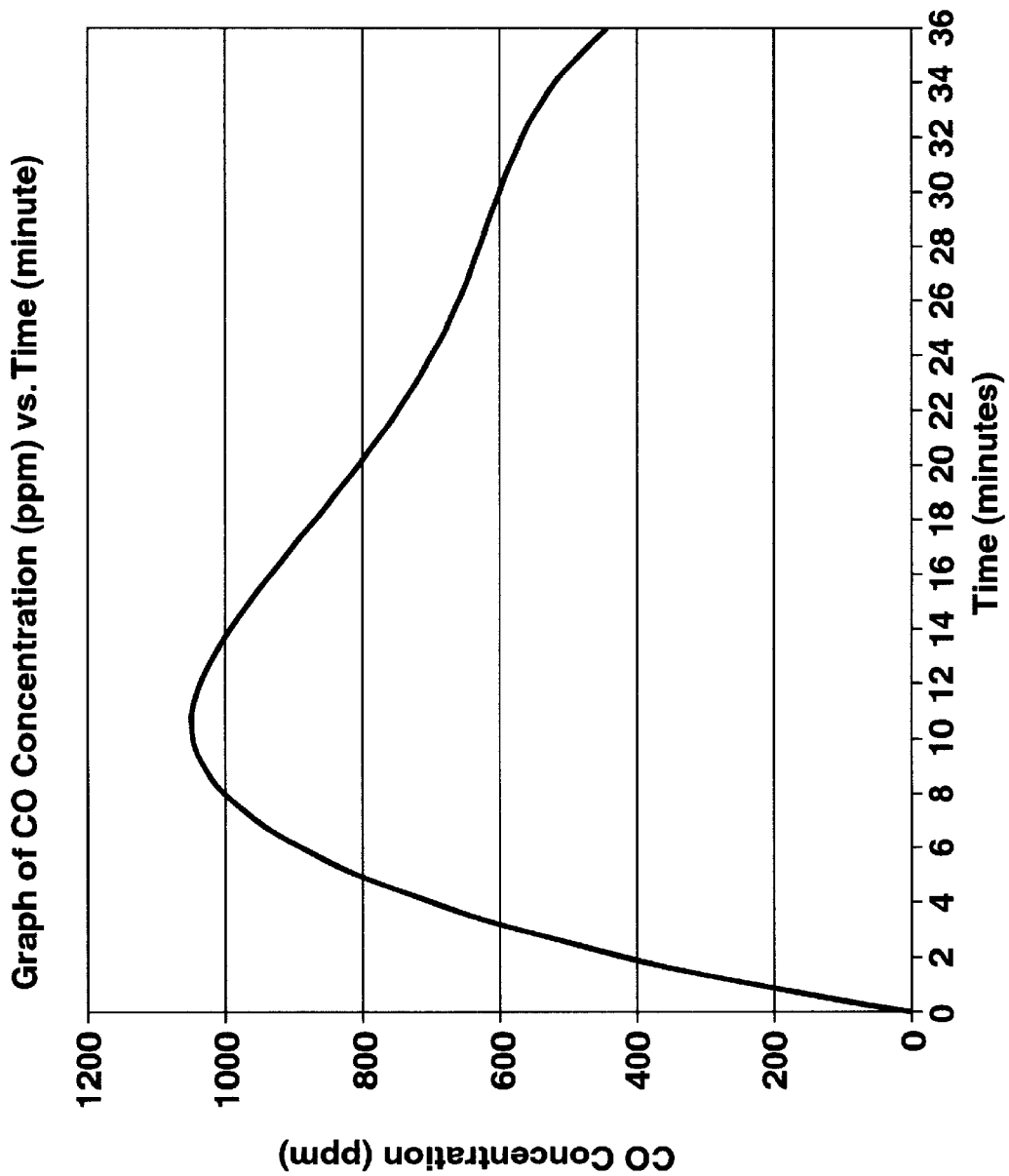
FIG. 4 is a graph of CO Concentration (ppm) vs. Time (minutes)

FIG. 4 is a graph of CO concentration (ppm) vs. Time (minutes), indicating that burning a charcoal pellet having a volume of 0.33 cubic meters in a chamber having an inner volume of $8 \times 10^{-3}$ cubic meters produces a CO concentration in excess of 400 ppm for over 36 minutes. This concentration of CO is sufficient to test whether a given CO alarm meets one of the UL 2034 standard test points based upon 10% carboxyhemoglobin, which requires a response time within 4–15 minutes, for a CO concentration above 400 ppm. Proportionally smaller portions of charcoal can be used for smaller volume chambers.

Figure 5:
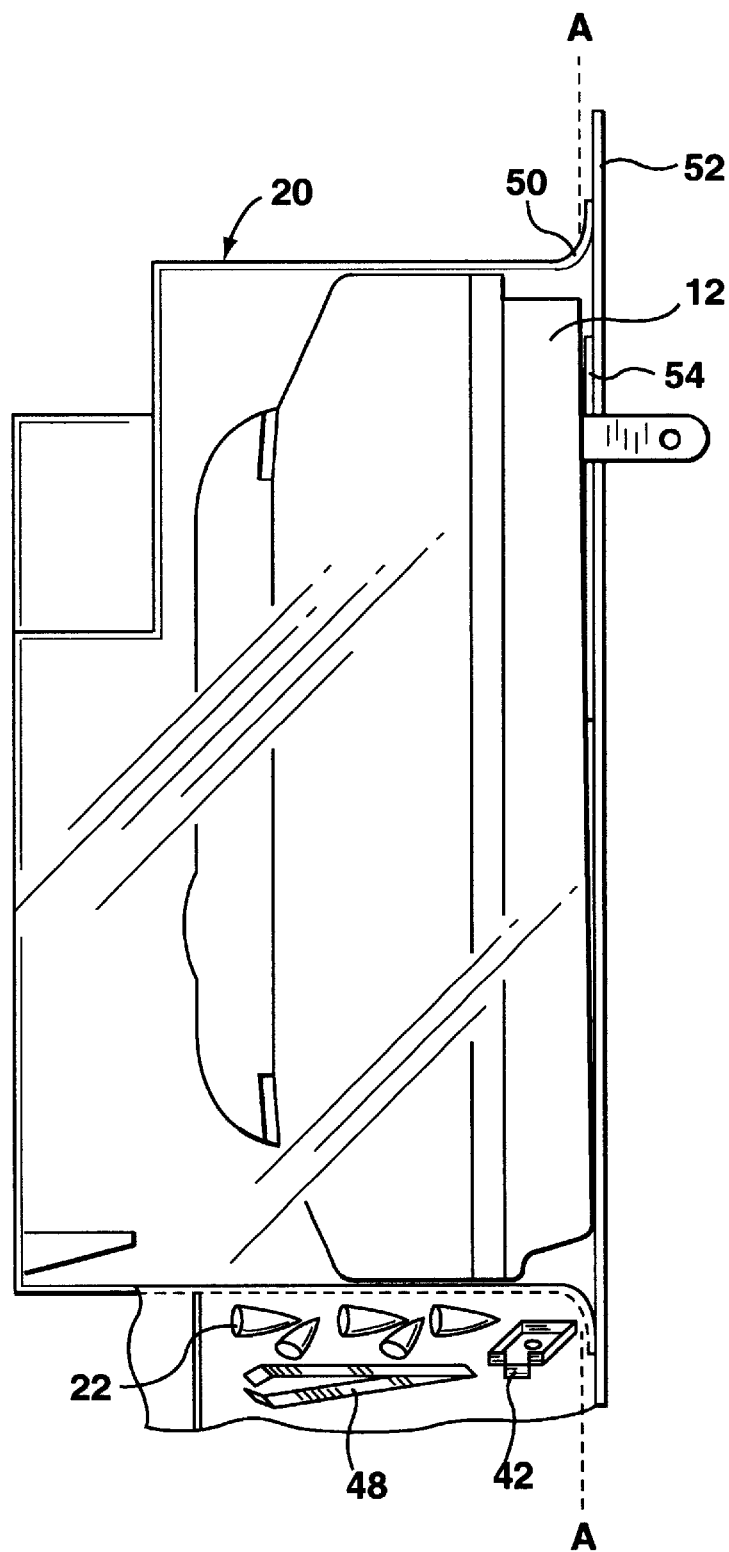
FIG. 5 is a side elevational view showing the preferred embodiment as part of the packaging for a CO alarm.

Referring now to FIG. 5, the test apparatus of the subject invention is preferably packaged and sold together with CO alarm 12, such that housing 20 forms part of the packaging for the alarm. As shown, housing 20 is formed with flared end portion 50 which is welded or glued onto cardboard backing 52 to form the clear plastic blister portion of a conventional blister pack containing CO alarm 12. Printed material 54 containing operating instructions and warranty information may be placed between the back of CO monitor 12 and cardboard backing 52. The package also includes a bottom compartment sized to hold fire box 42, tongs 48, and a supply of CO sources 22. When the blister pack is opened, flared end portion 50 can be removed from housing 20 by cutting along line A—A.

Referring again to FIGS. 1–3, test apparatus 10 may be used to test the operation of CO alarm 12, as follows. If fire box 42 is already in place in slot 44, CO source 22 may be grasped by tongs 48, and ignited, using a match or lighter, and then placed in fire box 42. Alternatively, fire box 42 may be removed from housing 20, CO source 22 may be placed in fire box 42 and then ignited, and fire box 42 inserted into slot 44 using tongs 48. Housing 20 is then fitted over alarm casing 14, by sliding sidewalls 28 over the periphery of casing 14. As CO source 22 smolders, sufficient CO gas will be generated within gas chamber 38 to trigger an alarm. Since the casings of conventional CO alarms are typically not airtight, some of the CO gas will leave chamber 38 through holes in the back of casing 14, and some fresh air will enter chamber 38. This air exchange must be taken into account, when determining the relative sizes of source 22 and chamber 38.

Figure 6:
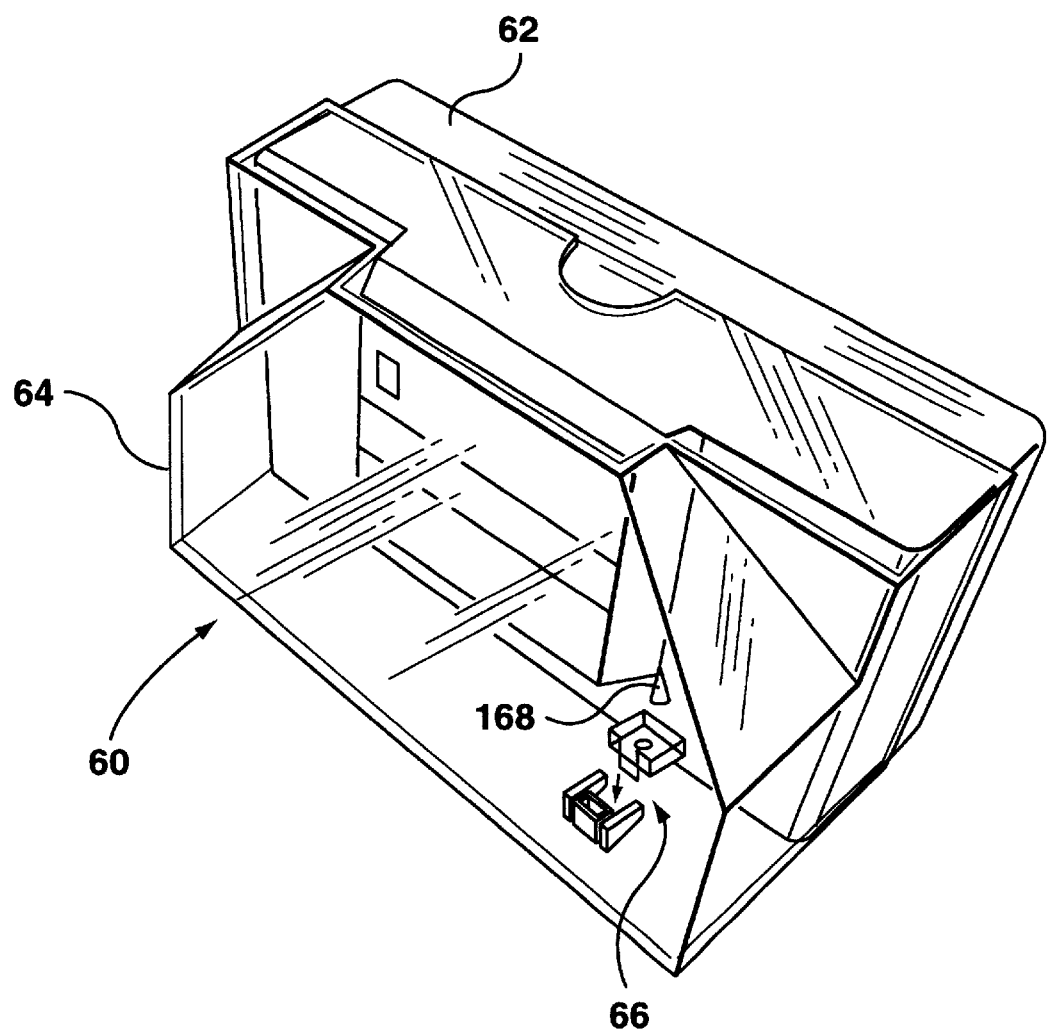
FIG. 6 is a front perspective view of an alternative embodiment of the subject invention, shaped to fit a rectangular CO alarm.
Figure 7:
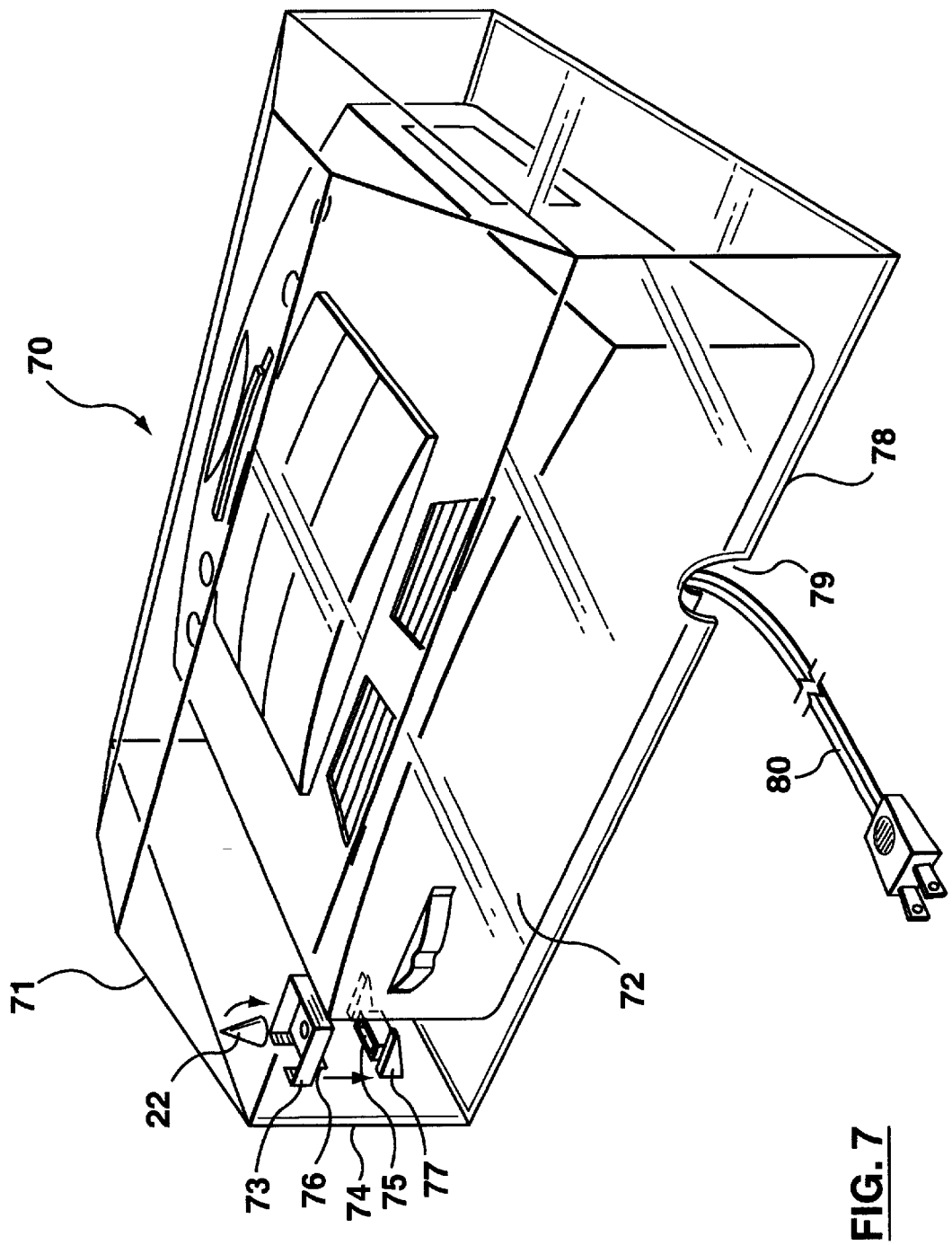
FIG. 7 is a rear perspective view of a further alternative embodiment of the subject invention, adapted for use with an alarm clock radio with integral CO alarm.
Figure 8:
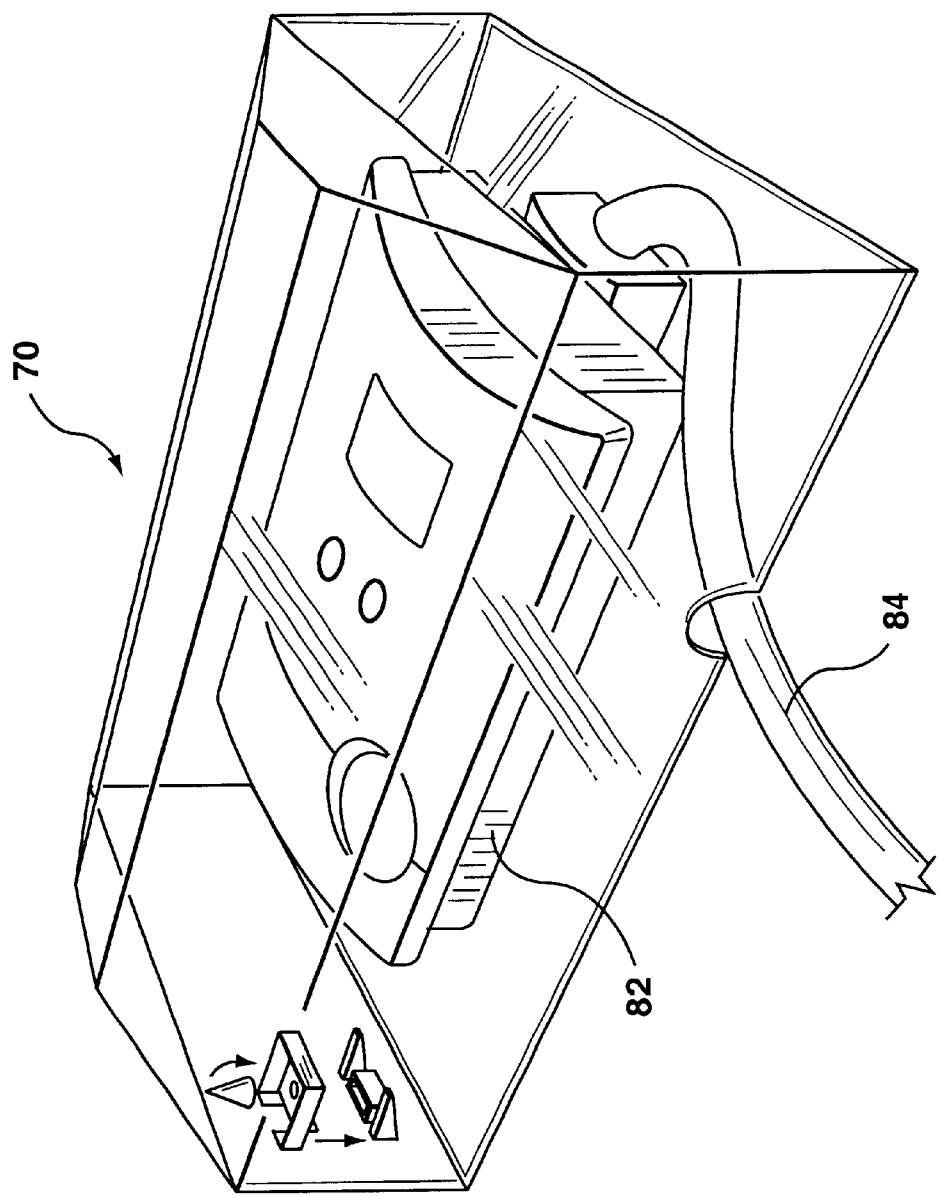
FIG. 8 is a rear perspective view of the alternative embodiment shown in FIG. 7, shown in use with another type of CO alarm.

Referring now FIGS. 6–8, the test apparatus of the subject invention can be configured to fit various different styles and types of CO alarms. As shown in FIG. 6, test apparatus 60 is sized and shaped to be friction fitted over the sides of rectangular CO alarm 62. Test apparatus 60 comprises housing 64 having source holder 66 shaped to hold CO source 68. Housing 64 forms a gas chamber which is sized relative to CO source 68 to ensure that the burning of CO source 68 will trigger a pre-selected alarm condition.

As shown in FIG. 7, in another alternative embodiment, test apparatus 70 comprises housing 71 sized and shaped to fit over clock radio/CO alarm 72, fire box 73, support means 77 extending inwardly from side wall 74, and CO source 22. Support means 77 is provided with slot 75 which is shaped to receive tang 76 of fire box 73. Housing 71 has a flat open bottom adapted to sit on a flat surface, and back wall 78 of housing 72 has a cutout 79 shaped to receive cord 80 of radio/alarm 72.

Referring now to FIG. 8, test apparatus 70 may also be used to test other types of CO alarms, such as alarm 82 having power line cord 84.

The subject invention accordingly provides a CO alarm testing kit which is inexpensive and easy to use. The subject test apparatus can be configured for use with various different types and brands of CO alarms. The subject test apparatus is inexpensive, and it can be reused by simply burning another charcoal pellet or piece of incense.

As shown in the figures, the housing of the subject test apparatus typically include a front cavity extension, which adds rigidity and aesthetic appeal to the housing. However, it should be understood that the housing could assume various other shapes, as long as the chamber formed thereby is suitable for generating an acceptable alarm condition.

It should therefore be understood that various modifications can be made to the preferred embodiments described and illustrated herein, without departing from the subject invention, the scope of which is defined in the appended claims.

What is claimed is:

1. A test apparatus for testing the operation of a carbon monoxide alarm of the type having a casing and a carbon monoxide sensor extending therefrom, comprising:

(a) a housing sized and configured to receive the casing and to form a gas chamber in communication with the sensor;

(b) a carbon monoxide source for generating a concentration of carbon monoxide within the gas chamber above a pre-selected threshold for a sufficient period of time to trigger an alarm condition, the carbon monoxide source comprising a flammable substance which generates carbon monoxide gas when burned;

(c) a holder located within the housing for holding the carbon monoxide source while the carbon monoxide source is being burned; and (d) wherein the holder comprises a metal fire box, sized to receive the flammable substance.

2. The apparatus defined in claim 1, wherein the holder also comprises support means extending into the gas chamber from a wall of the housing for supporting the fire box.

3. The apparatus defined in claim 2 wherein the support means comprises a protrusion extending horizontally along the wall of the housing having a slot sized to receive the fire box.

4. The apparatus defined in claim 3, wherein the fire box comprises a tab extending therefrom sized to fit within the slot.

5. The apparatus defined in claim 2, wherein the support means also comprises support brackets extending inwardly from the wall of the housing.

6. The apparatus defined in claim 5, wherein the sufficient period of time is in excess of 15 minutes.

7. An apparatus for packaging and testing the operation of a carbon monoxide alarm of the type having a casing and a carbon monoxide sensor extending therefrom comprising:

(a) a housing sized and configured to receive the casing and to form a gas chamber in communication with the sensor;

(b) a carbon monoxide source for generating a concentration of carbon monoxide within the gas chamber above a pre-selected threshold for a sufficient period of time to trigger an alarm condition, the carbon monoxide source comprising a flammable substance which generates carbon monoxide gas when burned;

(c) a holder located within the housing for holding the carbon monoxide source while the carbon monoxide source is being burned;

(d) wherein the housing forms a portion of the packaging for the carbon monoxide alarm; and (e) wherein the packaging is a blister pack comprising a plastic blister portion welded to a cardboard backing and the housing comprises the blister portion.

\* \* \* \* \*